United States Patent
Locke et al.

(10) Patent No.: US 11,083,629 B2
(45) Date of Patent: *Aug. 10, 2021

(54) RE-EPITHELIALIZATION WOUND DRESSINGS AND SYSTEMS

(71) Applicant: KCI Licensing, Inc., San Antonio, TX (US)

(72) Inventors: Christopher Brian Locke, Bournemouth (GB); Timothy Mark Robinson, Shillingstone (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 317 days.

This patent is subject to a terminal disclaimer.

(21) Appl. No.: 16/039,111

(22) Filed: Jul. 18, 2018

(65) Prior Publication Data

US 2018/0318138 A1     Nov. 8, 2018

Related U.S. Application Data

(60) Continuation of application No. 14/171,165, filed on Feb. 3, 2014, now Pat. No. 10,052,236, which is a
(Continued)

(51) Int. Cl.
*A61F 13/00* (2006.01)
*A61F 13/02* (2006.01)
(Continued)

(52) U.S. Cl.
CPC ...... *A61F 13/00068* (2013.01); *A61F 13/022* (2013.01); *A61F 13/0213* (2013.01);
(Continued)

(58) Field of Classification Search
CPC combination set(s) only.
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Guy K Townsend

(57) ABSTRACT

Methods, apparatuses, and systems for promoting re-epithelialization as an aspect of wound healing are presented. A re-epithelialization dressing for use with reduced pressure has a moist tissue-interface layer, a manifold member, and a sealing member. The moist tissue-interface layer has a plurality of apertures. The moist tissue-interface layer is for disposing adjacent to the wound and provides a moisture balance (i.e., provides moisture when the wound is dry and receives moisture when the wound site is substantially wet). The reduced pressure, apertures, and moist tissue-interface layer help with liquid management and otherwise promote re-epithelialization. Other systems, apparatuses, and methods are presented.

21 Claims, 3 Drawing Sheets

Related U.S. Application Data division of application No. 12/857,100, filed on Aug. 16, 2010, now Pat. No. 8,690,844.

(60) Provisional application No. 61/237,486, filed on Aug. 27, 2009.

(51) Int. Cl.
*A61M 1/00* (2006.01)
*A61M 27/00* (2006.01)

(52) U.S. Cl.
CPC ............ *A61M 1/0023* (2013.01); *A61M 1/90* (2021.05); *A61F 2013/0054* (2013.01); *A61F 2013/00174* (2013.01); *A61F 2013/00536* (2013.01); *A61F 2013/00748* (2013.01); *A61F 2013/00855* (2013.01); *A61M 27/00* (2013.01)

(56) References Cited

U.S. PATENT DOCUMENTS

| | | | |
|---|---|---|---|
| 2,632,443 A * | 3/1953 | Lesher | A61F 13/00021 128/888 |
| 2,682,873 A * | 7/1954 | Evans | A61F 13/00029 602/42 |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower Guiles, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A * | 11/1980 | Lock | A61F 13/00017 521/51 |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A * | 12/1987 | McNeil | A61M 1/0023 604/31 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A * | 3/1990 | Reed | A61F 13/023 604/307 |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,018,515 A * | 5/1991 | Gilman | A61F 13/0276 602/45 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,106,629 A * | 4/1992 | Cartmell | A61F 13/023 424/445 |
| 5,134,994 A | 8/1992 | Say | |
| 5,149,331 A | 9/1992 | Ferdman et al. | |
| 5,160,315 A * | 11/1992 | Heinecke | A61F 13/023 602/57 |
| 5,167,613 A * | 12/1992 | Karami | A61F 13/0203 602/42 |
| 5,176,663 A * | 1/1993 | Svedman | A61F 13/0203 128/888 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A * | 3/1994 | Komatsuzaki | A61F 13/00021 424/444 |
| 5,342,376 A | 8/1994 | Ruff | |
| 5,344,415 A | 9/1994 | DeBusk et al. | |
| 5,356,372 A * | 10/1994 | Donovan | A61F 13/023 602/41 |
| 5,358,494 A | 10/1994 | Svedman | |
| 5,423,737 A * | 6/1995 | Cartmell | A61F 13/023 602/57 |
| 5,437,622 A | 8/1995 | Carlon | |
| 5,437,651 A * | 8/1995 | Todd | A61M 1/0088 15/420 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A * | 6/1997 | Argenta | A61M 1/0088 128/897 |
| 5,645,081 A | 7/1997 | Argenta et al. | |
| 5,844,013 A * | 12/1998 | Kenndoff | C08G 18/08 521/137 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 * | 2/2002 | Heaton | A61F 13/023 128/897 |
| 6,420,622 B1 * | 7/2002 | Johnston | A47L 9/02 428/167 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,566,575 B1 * | 5/2003 | Stickels | A61F 13/023 602/41 |
| 6,685,681 B2 * | 2/2004 | Lockwood | A61M 1/0058 502/43 |
| 6,814,079 B2 | 11/2004 | Heaton et al. | |
| 7,004,915 B2 * | 2/2006 | Boynton | A61M 1/0037 601/6 |
| 7,070,584 B2 * | 7/2006 | Johnson | A61M 1/0088 424/444 |

(56) References Cited

U.S. PATENT DOCUMENTS

| | | | |
|---|---|---|---|
| 7,651,484 B2* | 1/2010 | Heaton | A61M 1/0031 604/313 |
| 7,790,945 B1* | 9/2010 | Watson, Jr. | A61M 27/00 602/43 |
| 7,846,141 B2 | 12/2010 | Weston | |
| 8,062,273 B2 | 11/2011 | Weston | |
| 8,172,816 B2* | 5/2012 | Kazala, Jr. | A61F 13/0223 604/313 |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,690,844 B2* | 4/2014 | Locke | A61F 13/00068 604/319 |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 10,052,236 B2* | 8/2018 | Locke | A61F 13/022 |
| 2001/0043943 A1* | 11/2001 | Coffey | A61F 13/02 424/447 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0132540 A1* | 9/2002 | Soerens | C08G 65/336 442/59 |
| 2002/0143286 A1 | 10/2002 | Tumey | |
| 2003/0203011 A1* | 10/2003 | Abuelyaman | A61K 6/90 424/445 |
| 2003/0232905 A1* | 12/2003 | Ives | C08K 5/0008 524/35 |
| 2004/0030304 A1* | 2/2004 | Hunt | A61L 15/22 604/317 |
| 2004/0243073 A1* | 12/2004 | Lockwood | A61M 1/0092 604/313 |
| 2005/0037194 A1* | 2/2005 | Greene | B29C 67/24 428/364 |
| 2005/0064021 A1* | 3/2005 | Rippon | A61L 26/0019 424/445 |
| 2005/0085795 A1* | 4/2005 | Lockwood | A61M 27/00 604/543 |
| 2005/0137539 A1* | 6/2005 | Biggie | A61M 1/0096 604/313 |
| 2005/0228329 A1* | 10/2005 | Boehringer | A61F 13/00021 602/52 |
| 2006/0041247 A1* | 2/2006 | Petrosenko | A61F 13/0203 604/543 |
| 2006/0155260 A1* | 7/2006 | Blott | A61F 13/00063 604/543 |
| 2006/0173253 A1* | 8/2006 | Ganapathy | A61B 5/1468 600/310 |
| 2006/0189910 A1* | 8/2006 | Johnson | A61F 13/0203 602/42 |
| 2006/0264796 A1* | 11/2006 | Flick | A61F 13/022 602/48 |
| 2007/0055209 A1* | 3/2007 | Patel | A61M 1/0088 604/315 |
| 2007/0185426 A1* | 8/2007 | Ambrosio | A61F 13/00068 602/43 |
| 2007/0219532 A1* | 9/2007 | Karpowicz | A61M 1/0029 604/540 |
| 2008/0011368 A1* | 1/2008 | Singh | A61M 39/1055 137/565.01 |
| 2008/0039763 A1* | 2/2008 | Sigurjonsson | A61F 13/022 602/56 |
| 2008/0076844 A1* | 3/2008 | Van Sumeren | B29C 67/202 521/137 |
| 2008/0215020 A1* | 9/2008 | Reeves | A61N 5/0616 604/305 |
| 2008/0300555 A1* | 12/2008 | Olson | A61F 13/0203 604/313 |
| 2009/0043268 A1* | 2/2009 | Eddy | A61M 1/0037 604/290 |
| 2009/0227969 A1* | 9/2009 | Jaeb | A61F 13/00063 604/313 |
| 2009/0254066 A1* | 10/2009 | Heaton | A61M 1/0052 604/543 |
| 2009/0275922 A1* | 11/2009 | Coulthard | A61M 1/0068 604/543 |
| 2009/0306630 A1* | 12/2009 | Locke | A61M 1/0001 604/543 |
| 2010/0125258 A1* | 5/2010 | Coulthard | A61M 1/0088 604/319 |
| 2011/0054422 A1* | 3/2011 | Locke | A61F 13/022 604/319 |
| 2011/0230848 A1* | 9/2011 | Manwaring | A61M 1/0088 604/290 |
| 2011/0288512 A1* | 11/2011 | Locke | B01D 53/268 604/319 |
| 2012/0016323 A1* | 1/2012 | Robinson | A61M 1/0088 604/319 |
| 2012/0046624 A1* | 2/2012 | Locke | A61M 1/0096 604/319 |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN January 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

RE-EPITHELIALIZATION WOUND DRESSINGS AND SYSTEMS

RELATED APPLICATION

This application is a continuation of U.S. patent application Ser. No. 14/171,165, filed Feb. 3, 2014, which is a divisional of U.S. patent application Ser. No. 12/857,100, filed Aug. 16, 2010, now U.S. Pat. No. 8,690,844, issued Apr. 8, 2014, which claims the benefit, under 35 USC § 119(e), of the filing of U.S. Provisional Patent Application Ser. No. 61/237,486, entitled "Re-Epithelialization Wound Dressings and Systems," filed Aug. 27, 2009. Each of the applications above are incorporated herein by reference for all purposes.

BACKGROUND

This disclosure relates generally to medical treatment systems and, more particularly but not by way of limitation, to re-epithelialization wound dressings and systems.

The physiological process of wound healing involves different phases that may occur simultaneously or sequentially. As used herein, "or" does not require mutual exclusivity. Two phases of the wound healing process involve granulation (proliferation) and re-epithelialization.

SUMMARY

Improvements to certain aspects of wound care dressings, methods, and systems are addressed by the present invention as shown and described in a variety of illustrative, non-limiting embodiments herein. According to an illustrative, non-limiting embodiment, a re-epithelialization dressing for use with reduced pressure includes a moist tissue-interface layer, a manifold member, and a sealing member. The moist tissue-interface layer is adapted to provide a moisture balance for the tissue and is formed with a plurality of apertures. The manifold is operable to distribute reduced pressure and is disposed between the sealing member and the moist tissue-interface layer.

According to another illustrative, non-limiting embodiment, a system for promoting re-epithelialization of a wound includes a re-epithelialization wound dressing. The re-epithelialization wound dressing includes a moist tissue-interface layer, a manifold member, and a sealing member. The moist tissue-interface layer is adapted to provide a moisture balance for the tissue and is formed with a plurality of apertures. The manifold is operable to distribute reduced pressure and is disposed between the sealing member and the moist tissue-interface layer. The system further includes a reduced-pressure connector, a reduced-pressure delivery conduit, and a reduced-pressure source to provide reduced pressure to the re-epithelialization wound dressing. The reduced-pressure delivery conduit is operable to fluidly couple the reduced-pressure source to the reduced-pressure connector.

According to another illustrative, non-limiting embodiment, a method for promoting re-epithelialization of a wound includes the steps of: deploying a re-epithelialization dressing proximate the wound; fluidly coupling a reduced-pressure delivery conduit to the re-epithelialization dressing; and providing reduced pressure to the reduced-pressure delivery conduit. The re-epithelialization dressing includes a moist tissue-interface layer operable to provide a moisture balance. The moist tissue-interface layer has a first side and a second, tissue-facing side and is formed with a plurality of apertures. The re-epithelialization dressing further includes a manifold member for distributing reduced pressure. The manifold member has a first side and a second, tissue-facing side. The re-epithelialization dressing also includes a sealing member, which has a first side and a second, tissue-facing side. The manifold member is disposed between the sealing member and the moist tissue-interface layer.

Other features and advantages of the illustrative embodiments will become apparent with reference to the drawings and detailed description that follow.

DETAILED DESCRIPTION

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
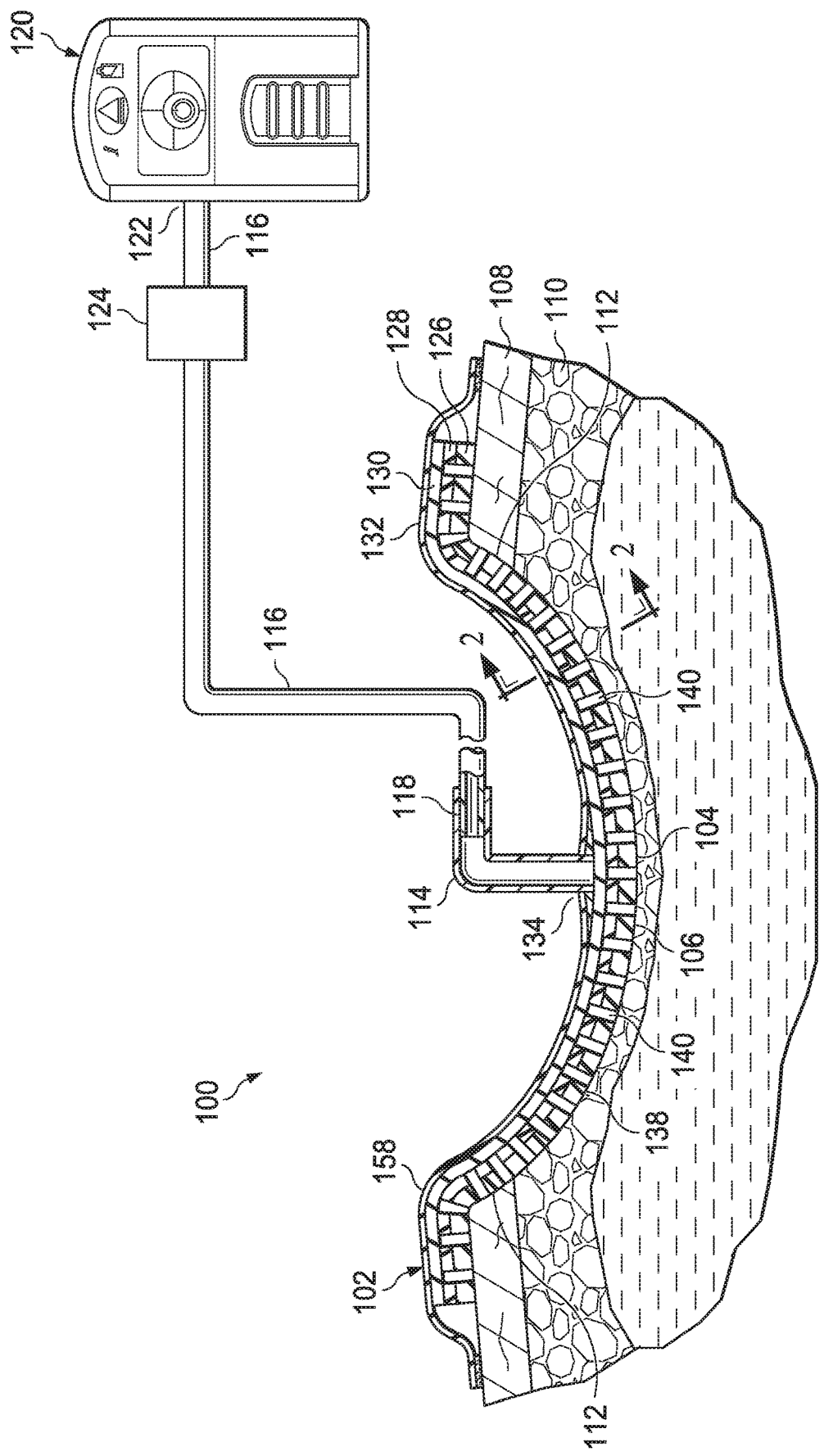
FIG. 1 is a schematic diagram with a portion in cross section of an illustrative, non-limiting embodiment of a system for treating a wound.

Referring primarily to FIG. 1, an illustrative, non-limiting embodiment of a wound treatment system 100, which includes a re-epithelialization dressing 102, is presented. The re-epithelialization dressing 102 is shown deployed for treatment on a tissue site 104 and in particular a wound 106, or wound site. The wound 106 is shown extending through epidermis 108 and into subcutaneous tissue 110. The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. The wound treatment system 100 with the re-epithelialization dressing 102 promotes re-epithelialization of the wound 106 and may encourage migration of wound edges 112.

The re-epithelialization, or epithelialization, phase of acute wound healing involves resurfacing of the wound 106 and changes in the wound edges 112. The process protects a patient's body from invasion by outside organisms and may occur concurrently with other phases if not restricted. The resurfacing aspect involves keratinocytes.

Among other things, keratinocytes form layers of the dermis and epidermis. Keratinocytes are derived from epidermal stem cells located in the bulge area of hair follicles and migrate from that location into the basal layers of epidermis. The keratinocytes proliferate and differentiate to produce epidermis and thereby replenish the epidermis. Keratinocytes may respond to signals released from growth factors, which may be in wound exudate, by advancing in a sheet to resurface a space. Because of this migration, a moist wound environment may speed or otherwise facilitate the migration of keratinocytes toward one another from the wound edges 112. The wound treatment system 100 promotes this re-epithelialization phase or process.

The wound treatment system 100 includes a reduced-pressure connector 114 that may be associated with the re-epithelialization dressing 102 for providing reduced pressure to at least a portion of the re-epithelialization dressing 102. A reduced-pressure delivery conduit 116 may be fluidly coupled to the reduced-pressure connector 114 at a first end 118 and fluidly coupled to a reduced-pressure source 120 at a second end 122. One or more devices 124 may be fluidly coupled between the reduced-pressure connector 114 and the reduced-pressure source 120, such as on the reduced-pressure delivery conduit 116.

The device or devices 124 that may be fluidly coupled to the reduced-pressure delivery conduit 116 include, for example, without limitation, a fluid reservoir (or collection member, to hold exudates and other fluids removed), a pressure-feedback device, a volume detection system, a blood detection system, an infection detection system, a flow monitoring system, a temperature monitoring system, or other device.

The reduced-pressure source 120 provides reduced pressure as a part of the wound treatment system 100. The term "reduced pressure" as used herein generally refers to a pressure less than the ambient pressure at the tissue site 104 that is being subjected to treatment. In most cases, this reduced pressure will be less than the atmospheric pressure at which the patient is located. Alternatively, the reduced pressure may be less than a hydrostatic pressure of tissue at the tissue site 104. Although the terms "vacuum" and "negative pressure" may be used to describe the pressure applied to the tissue site, the actual pressure applied to the tissue site may be significantly more than the pressure normally associated with a complete vacuum. Unless otherwise indicated, values of pressure stated herein are gauge pressures.

The reduced pressure delivered by the reduced-pressure source 120 may be constant or varied (patterned or random) and may be delivered continuously or intermittently. In order to maximize patient mobility and ease, the reduced-pressure source 120 may be a battery-powered, reduced-pressure generator. This facilitates application in the operating room and provides mobility and convenience for the patient during the rehabilitation phase. Other sources of reduced pressure may be utilized, such as V.A.C.® therapy unit, which is available from KCI of San Antonio, Tex., wall suction, or a mechanical unit.

The reduced pressure developed by the reduced-pressure source 120 is delivered through the reduced-pressure delivery conduit 116, or medical conduit or tubing, to the reduced-pressure connector 114. An interposed hydrophobic membrane filter may be interspersed between the reduced-pressure delivery conduit 116 and the reduced-pressure source 120. In another illustrative, non-limiting embodiment (not shown), the reduced-pressure source may be contained within the re-epithelialization dressing 102 and may be, for example, a micro-pump.

Figure 2:
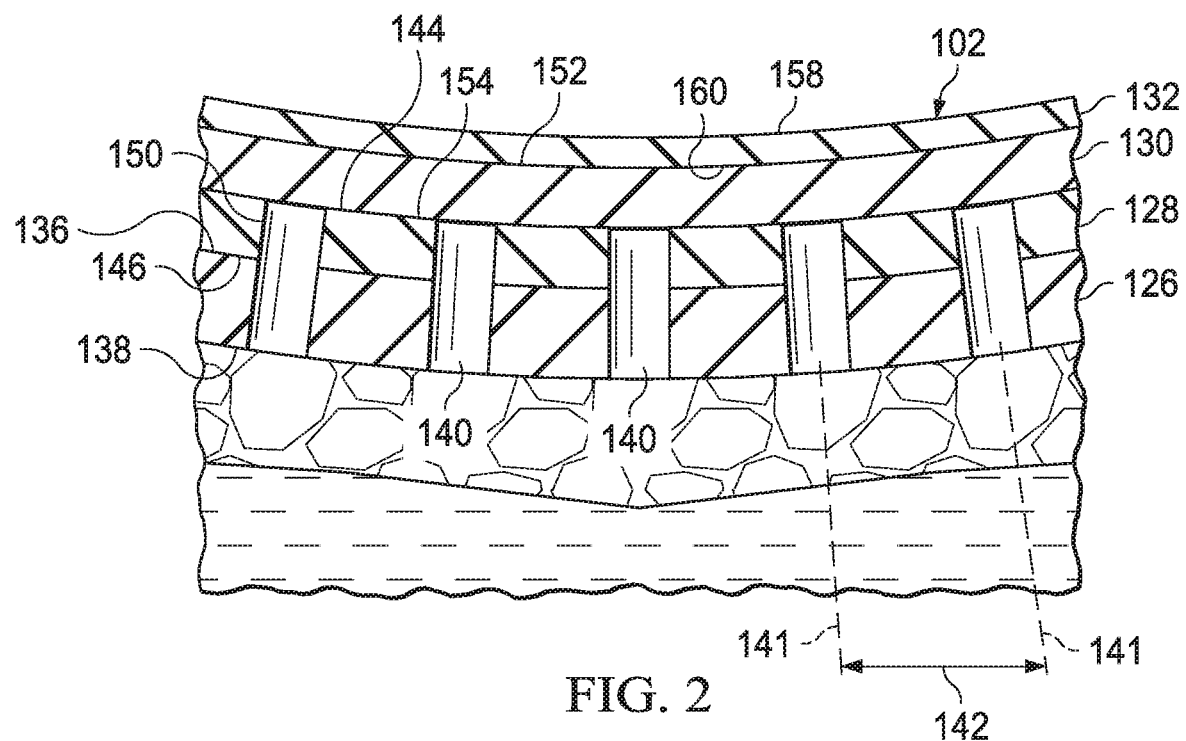
FIG. 2 is a schematic detail of a portion of the illustrative, non-limiting embodiment of a system for treating a wound of FIG. 1 shown without reduced pressure applied.

Referring now primarily to FIGS. 1 and 2, the re-epithelialization dressing 102 may include a plurality of layers or materials. For example, the re-epithelialization dressing 102 may include a moist tissue-interface layer 126, a support layer 128, a manifold member 130, and a sealing member 132. The sealing member 132 may be formed with a connector aperture 134 through which at least a portion of the reduced-pressure connector 114 extends. In the illustrative, non-limiting embodiment of FIG. 1, the reduced-pressure connector 114 is shown disposed in part between the sealing member 132 and the manifold member 130 and with a portion extending through the connector aperture 134. The re-epithelialization dressing 102 may have additional layers or fewer layers and the layers may be placed in differing combinations in some embodiments.

The moist tissue-interface layer 126 has a first side 136 and a second, tissue-facing side 138. The moist tissue-interface layer 126 is formed with a first plurality of apertures 140, which may take any shape. The first plurality of apertures 140 extend through the moist tissue-interface layer 126. The first plurality of apertures 140 may be formed with a laser, punched, drilled, or formed by casting, or any other technique. The first plurality of apertures 140 may be formed with a uniform pattern or may be random and may have uniform or varied diameters.

In one illustrative, non-limiting embodiment, the first plurality of apertures 140 are formed with a uniform pattern with aperture centers 141 being formed with a distance 142 between adjacent aperture centers 141. In some illustrative, non-limiting embodiments, the distance 142 is about two millimeters, three millimeters, four millimeters, five millimeters, six millimeters, seven millimeters, eight millimeters, nine millimeters, ten millimeters, or more. The distance 142 may be selected for the desired liquid transmission through the moist tissue-interface layer 126. The diameter of the first plurality of apertures 140 may also be selected so that when reduced pressure is applied and saturation occurs (at least in some embodiments), the first plurality of apertures 140 will not firmly collapse and seal but will become restricted to allow liquid to pass but to generally restrict the passing of gases through the first plurality of apertures 140. In other embodiments, the first plurality of apertures 140 may be sized to allow the first plurality of apertures 140 to close completely and firmly under the influence of reduced pressure.

The moist tissue-interface layer 126 may be made from numerous materials. The moist tissue-interface layer 126 may be, for example, a water-based material, such as a hydrogel or hydrocolloid. The material from which the moist tissue-interface layer 126 is formed provides a fluid balance, or equilibrium, with respect to a desired moist condition. Thus, for example, the material may provide moisture when needed (i.e., the tissue site 104 is dry) and will absorb moisture when needed (i.e., excessive moisture exists at the tissue site 104 or the tissue site 104 is substantially wet). The second, tissue-facing side 138 may be a relatively smooth surface as compared to a micro-strain inducing material, such as an open-cell foam. The relatively smooth surface of the second, tissue-facing side 138 helps to promote (or at least not hinder) cell migration. The relatively smooth surface of the second, tissue-facing side 138 may create little or no local micro-strain. The moist environment provided by the moist tissue-interface layer 126, fluid management of the first plurality of apertures 140, and the relatively smooth surface of the second, tissue-facing side 138 may encourage re-epithelialization of the wound 106.

In other illustrative, non-limiting embodiments, other materials may be used for the moist tissue-interface layer 126, such as a very dense hydrophilic foam (e.g., a hydrophilic closed cell foam); a film-coated, perforated, non-woven material; a hydrogel-impregnated foam; a hydroactive dressing material, or other material. The hydrogel-impregnated foam may be particularly well suited for deeper wounds or difficult shapes. The moist tissue-interface layer 126 may be perforated or cut into sections that allow removal of one or more portions of the moist tissue-interface layer 126 in order to provide reduced pressure to a portion or the tissue site 104. An opening created by the removed section may help with a highly exudating wound or may promote granulation if desired in an area of the wound 106.

Figure 3:
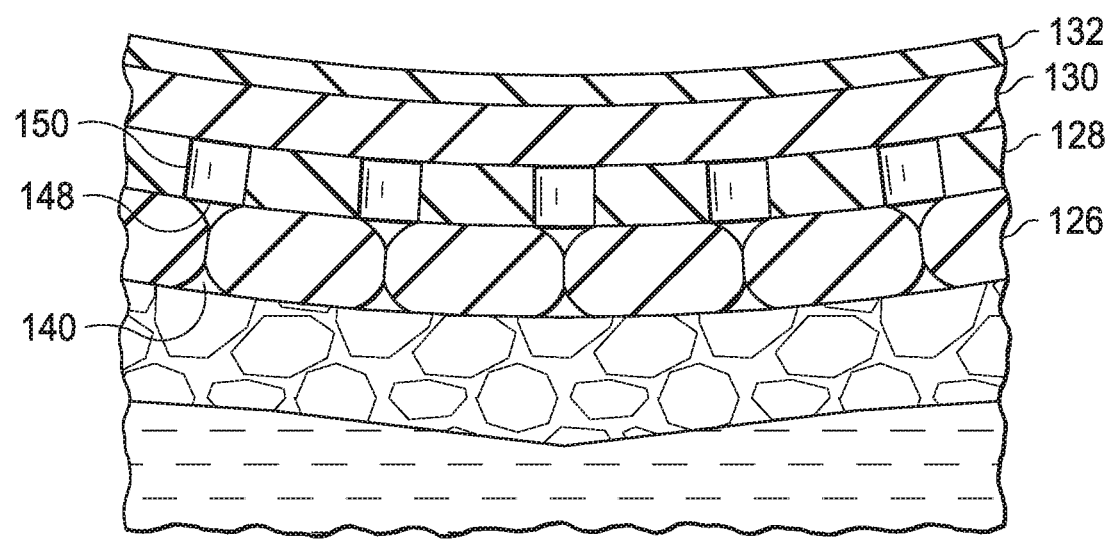
FIG. 3 is a schematic detail of a portion of the illustrative, non-limiting embodiment of a system for treating a wound of FIG. 1 shown with reduced pressure applied.

In use, the moist tissue-interface layer 126 will typically swell as the moist tissue-interface layer 126 receives fluid under reduced pressure. With sufficient fluid, the moist tissue-interface layer 126 may become saturated. As shown in FIG. 3, the first plurality of apertures 140 may substantially swell to a restricted position, or state, as compared to the open position, or state, of FIG. 2. The restricted position occurs when the moist tissue-interface layer 126 is substantially saturated. In the restricted position, the first plurality of apertures 140 will allow liquid to pass from the tissue site 104 through the first plurality of apertures 140 but will not substantially communicate reduced pressure through the first plurality of apertures 140. Other portions of the re-epithelialization dressing 102 will remove fluid from the first side 136 of the moist tissue-interface layer 126 once the moist tissue-interface layer 126 becomes saturated or substantially saturated. Some liquids or moisture, e.g., exudates, will remain at the wound 106 and may possibly assist in the healing process by providing signals.

The re-epithelialization dressing 102 may include an optional support layer 128. The support layer 128 has a first side 144 and a second, tissue-facing side 146. The second, tissue-facing side 146 is disposed adjacent to the first side 136 of the moist tissue-interface layer 126. The moist tissue-interface layer 126 and the support layer 128 may be coupled. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. The term "coupled" may include any known technique, including, without limitation, welding (e.g., ultrasonic or RF welding), bonding, adhesives, cements, or other techniques or devices. Fluid coupling means that fluid is in communication between the designated parts or locations.

The support layer 128 is optional but may be added to provide support for the moist tissue-interface layer 126. As shown best by comparing FIGS. 2 and 3, the support layer 128 may help hold a first end 148 of the first plurality of apertures 140 in an open position or with a set diameter while other portions may be further restricted as part of the restricted state. The support layer 128 may be formed from numerous materials, such as an occlusive film material. The support layer 128 may be, for example, a polyurethane layer, a polyethylene layer, or other support material. The support layer 128 may help direct fluid flow and provide support, particularly for the first plurality of apertures 140, as previously mentioned. The support layer 128 may be formed with a second plurality of apertures 150. The second plurality of apertures 150 may align and correspond with the first plurality of apertures 140. The second plurality of apertures 150 may be formed in the same or similar manner as the first plurality of apertures 140.

The re-epithelialization dressing 102 includes the manifold member 130. The manifold member 130 has a first side 152 and a second, tissue-facing side 154. The manifold member 130 may be formed from any material that distributes fluids, including reduced pressure. The term "manifold" as used herein generally refers to a substance or structure that is provided to assist in applying reduced pressure to, delivering fluids to, or removing fluids from a tissue site 104. The manifold member 130 typically includes a plurality of flow channels or pathways that distribute fluids provided to and removed from the tissue site 104 around the manifold member 130. In one illustrative, non-limiting embodiment, the flow channels or pathways are interconnected to improve distribution of fluids provided or removed from the tissue site 104.

The manifold member 130 may include, for example, without limitation, devices that have structural elements arranged to form flow channels, such as, for example, cellular foam, open-cell foam, porous tissue collections, liquids, gels, and foams that include, or cure to include, flow channels. The manifold member 130 may be porous and may be made from foam, gauze, felted mat, or any other material suited to a particular biological application. In one illustrative, non-limiting embodiment, the manifold member 130 is a porous foam and includes a plurality of interconnected cells or pores that act as flow channels. The porous foam may be a polyurethane, open-cell, reticulated foam, such as GranuFoam® material manufactured by Kinetic Concepts, Incorporated of San Antonio, Tex. Other embodiments may include "closed cells." In one non-limiting illustration, a manifold member 130 is formed of a non-woven material, such as a non-woven material available from Libeltex BVBA of Belgium. The second, tissue-facing side 154 of the manifold member 130 is disposed adjacent to the first side 144 of the support layer 128 in one illustrative, non-limiting embodiment or adjacent to the first side 136 of the moist tissue-interface layer 126 in another illustrative, non-limiting embodiment.

The re-epithelialization dressing 102 includes the sealing member 132. The sealing member 132 has a first side 158 and a second, tissue-facing side 160. The sealing member 132 forms a sealed space over the tissue site 104 or wound 106. The second, tissue-facing side 160 is disposed adjacent to and may be coupled to the first side 152 of the manifold member 130 or another layer. The sealing member 132 may be formed from any material that provides a fluid seal. "Fluid seal," or "seal," means a seal adequate to maintain reduced pressure at a desired site given the particular reduced-pressure source or subsystem involved. The sealing member may, for example, be an impermeable or semi-permeable, elastomeric material. "Elastomeric" means having the properties of an elastomer. Elastomeric generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional examples of sealing member materials include a silicone drape, 3M Tegaderm® drape, acrylic drape, such as one available from Avery Dennison, or an incise drape.

Figure 4:
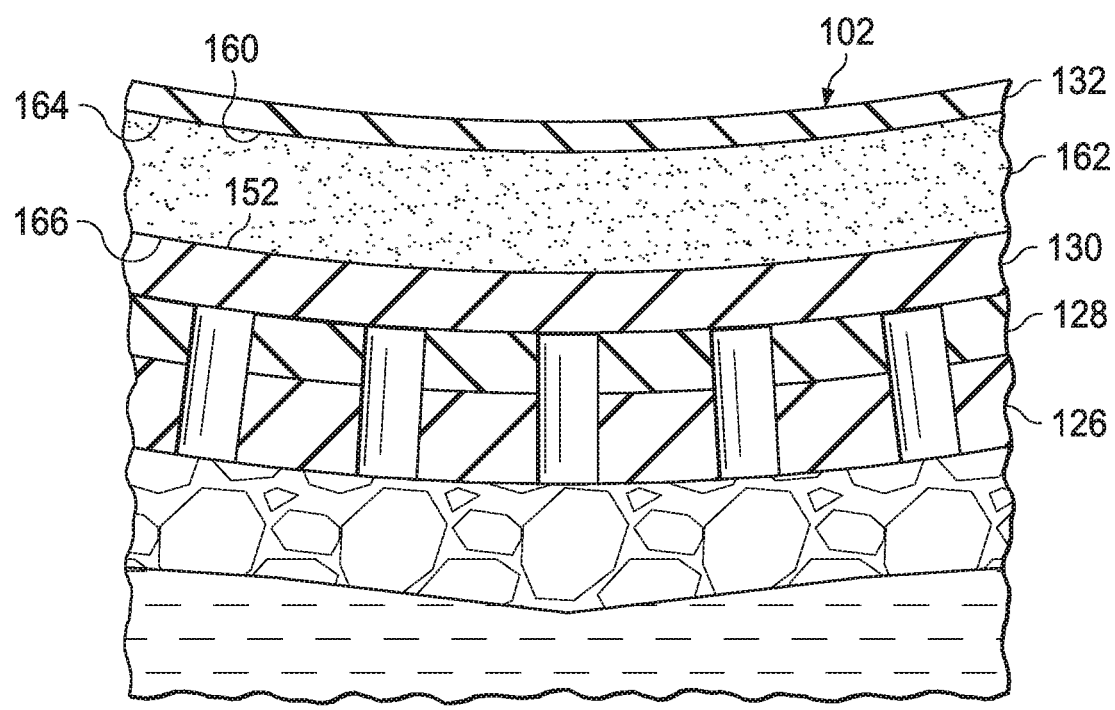
FIG. 4 is a schematic detail of a portion of the illustrative, non-limiting embodiment of a system for treating a wound of FIG. 1 shown with an absorber layer added.

Referring now primarily to FIG. 4, the re-epithelialization dressing 102 may have an optional absorbent layer 162, or absorber, disposed between the sealing member 132 and the manifold member 130 or other layers. The absorbent layer 162 has a first side 164 and a second, tissue-facing side 166. The first side 164 may be coupled to the second, tissue-facing side 160 of the sealing member 132 and the second, tissue-facing side 166 of the absorbent layer 162 may be coupled to the first side 152 of the manifold member 130. The absorbent layer 162 functions primarily to store or maintain fluids. The absorbent layer 162 may be formed from super-absorbent polymers (SAP) or other materials suited for retaining fluids within the re-epithelialization dressing 102. The material and thickness of the material forming the absorbent layer 162 may be selected based on the desired quantity of fluid to be retained. The absorbent layer 162 may be formed from one or more constituent layers.

In operation, according to an illustrative, non-limiting embodiment, the tissue site 104, and in particular the wound 106, may be treated with the wound treatment system 100 by deploying the re-epithelialization dressing 102. The re-epithelialization dressing 102 is placed adjacent to the wound 106 and a portion of the patient's intact epidermis 108. If not already installed, the reduced-pressure connector 114 is fluidly coupled to the re-epithelialization dressing 102 to provide reduced pressure and, if not already deployed, the sealing member 132 is deployed over other portions of the re-epithelialization dressing 102. The second, tissue-facing side 138 of the moist tissue-interface layer 126 is thus disposed adjacent to the wound 106 and a portion of the intact epidermis 108 as shown in FIG. 1. The second, tissue-facing side 138 presents a moist, smooth surface to the wound 106 and the wound edges 112.

If not already installed, the reduced-pressure delivery conduit 116 is fluidly coupled to the reduced-pressure connector 114 and to the reduced-pressure source 120. The reduced-pressure source 120 is activated and reduced pressure is thereby supplied to the re-epithelialization dressing 102. The reduced pressure may help to hold the re-epithelialization dressing 102 in situ, may help avoid any fluid leaks from the re-epithelialization dressing 102, may help avoid infection, and may help to manage fluids.

Typically, the reduced pressure provided to the re-epithelialization dressing 102 is in the range of −10 to −100 mm Hg and more typically in the range of −25 to −75 mm Hg. The reduced pressure is adequate to cause a flow of fluid, but is not typically high enough to cause substantial micro-strain at the tissue site 104. In other illustrative, non-limiting embodiments, the reduced pressure may be between the range of −10 mm Hg and −200 mm Hg. In other illustrative, non-limiting embodiment, the reduced pressure may be in the range of −100 to −200 mm Hg for an initial time period and then be in the range of −25 to −100 mm Hg for a second time period. Other variations are possible as desired.

When reduced pressure is provided to the re-epithelialization dressing 102, the first plurality of apertures 140 may go immediately or over time with saturation from an open position (FIG. 2) to a restricted position or state (FIG. 3). In the restricted state, the first plurality of apertures 140 may allow liquids to pass, but prevent or restrict gases (and gaseous pressure) from being transmitted. The re-epithelialization dressing 102 may thereby exert a force on the tissue site 104 without communicating gaseous pressure. If included, the support layer 128 may hold the first end 148 of the first plurality of apertures 140 substantially open or with a constant diameter.

The reduced pressure delivered to the re-epithelialization dressing 102 helps to remove excess fluids from the tissue site 104 and helps to remove fluids from the moist tissue-interface layer 126 when the moist tissue-interface layer 126 becomes substantially saturated. The fluid balance, or equilibrium, of the moist tissue-interface layer 126 also helps manage fluid in that the moist tissue-interface layer 126 provides fluid when the tissue site 104 is dry or helps absorb fluids when the tissue site 104 is wet. The fluid removal by the moist tissue-interface layer 126 may be slowly accomplished to allow some exudate (but not pooling of exudate) to remain at the tissue site 104 to facilitate the healing process. The exudate may help by allowing signaling (e.g., from growth factors) to activate keratinocytes as previously mentioned.

The moist tissue-interface layer 126 also provides a relatively smooth surface against the tissue site 104 that may facilitate (or at least not inhibit) cell migration. In addition to providing a relatively smooth moist surface, the moist tissue-interface layer 126 may be left for extended periods of time against the tissue site 104 without granulation in-growth, infection, or the need for frequent dressing changes.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

We claim:

1. A re-epithelialization dressing for use with reduced pressure to treat a wound site, the dressing comprising:
    a moist tissue-interface layer for disposing adjacent to the wound site, the moist tissue-interface layer providing a moisture balance, the moist tissue-interface layer having a first side and a second, tissue-facing side, wherein a plurality of apertures are formed through the moist tissue-interface layer, and wherein each of the plurality of apertures extends through the moist tissue-interface layer between the first side and the second, tissue-facing side of the moist tissue-interface layer;
    a foam manifold member for distributing reduced pressure, the manifold member having a first side and a second, tissue-facing side;
    a sealing member, the sealing member having a first side and a second, tissue-facing side; and
    wherein the manifold member is disposed between the sealing member and the moist tissue-interface layer.

2. The re-epithelialization dressing of claim 1, wherein the plurality of apertures are operable, under the influence of increasing moisture, to move from an open position to a restricted position, and wherein, in the restricted position, the plurality of apertures allows liquid to pass and restricts gas from passing.

3. The re-epithelialization dressing of claim 1, wherein the moist tissue-interface layer comprises a hydrogel layer.

4. The re-epithelialization dressing of claim 1, wherein the moist tissue-interface layer comprises a hydrocolloid layer.

5. The re-epithelialization dressing of claim 1, wherein the moist tissue-interface layer comprises a hydrogel-impregnated foam layer.

6. The re-epithelialization dressing of claim 1, further comprising a support layer having a first side and a second-tissue facing side, wherein the second-tissue facing side of the support layer is disposed adjacent to the first side of the moist tissue-interface layer.

7. The re-epithelialization dressing of claim 1, further comprising a support layer having a first side and a second-tissue facing side, wherein the second-tissue facing side of the support layer is coupled to the first side of the moist tissue-interface layer.

8. The re-epithelialization dressing of claim 1, further comprising an absorbent layer disposed between the manifold member and the sealing member.

9. The re-epithelialization dressing of claim 1, further comprising: a support layer having a first side and a second-tissue facing side, wherein the second-tissue facing side of the support layer is disposed adjacent to the first side of the moist tissue-interface layer; and an absorbent layer disposed between the first side of the manifold member and the second, tissue-facing side of the sealing member.

10. The re-epithelialization dressing of claim 1,
wherein the second, tissue-facing side of the moist tissue-interface layer is disposed adjacent to the wound site;
wherein the second, tissue-facing side of the manifold is disposed adjacent to the first side of the moist tissue-interface layer;
wherein the second, tissue-facing side of the sealing member is disposed adjacent to the first side of the manifold member; and
wherein the plurality of apertures in the moist tissue-interface layer are spaced by at least one millimeter between centers.

11. A system for promoting re-epithelialization of a wound, the system comprising:
a re-epithelialization wound dressing comprising:
a moist tissue-interface layer operable to provide a moisture balance and including a first side and a second, tissue-facing side that presents a smooth surface configured to contact both the wound and intact epidermis around the wound to prevent granulation in-growth, wherein a plurality of perforations are formed through the moist tissue-interface layer between the first side and the second, tissue-facing side of the moist tissue-interface layer,
a foam manifold member for distributing reduced pressure, the manifold member having a first side and a second, tissue-facing side,
a sealing member, the sealing member having a first side and a second, tissue-facing side, and
wherein the manifold member is disposed between the sealing member and the moist tissue-interface layer; and
a reduced-pressure source fluidly coupled to the manifold member.

12. The system of claim 11,
wherein the plurality of perforations are operable, under the influence of increasing moisture, to move from an open position to a restricted position, and
wherein, in the restricted position, the plurality of perforations allows liquid to pass and restricts gas from passing.

13. The system of claim 11, wherein the moist tissue-interface layer comprises a hydrogel layer.

14. The system of claim 11, wherein the moist tissue-interface layer comprises a hydrocolloid layer.

15. The system of claim 11, wherein the moist tissue-interface layer comprises a hydrogel-impregnated foam layer.

16. The system of claim 11, further comprising a support layer having a first side and a second-tissue facing side, wherein the second, tissue-facing side of the support layer is disposed adjacent to the first side of the moist tissue-interface layer.

17. The system of claim 11, further comprising a support layer having a first side and a second-tissue facing side, wherein the second-tissue facing side of the support layer is coupled to the first side of the moist tissue-interface layer.

18. The system of claim 11, further comprising an absorbent layer disposed between the manifold member and the sealing member.

19. The system of claim 11, further comprising: a support layer having a first side and a second-tissue facing side, wherein the second-tissue facing side of the support layer is disposed adjacent to the first side of the moist tissue-interface layer; and an absorbent layer disposed between the first side of the manifold member and the second, tissue-facing side of the sealing member.

20. The system of claim 11, wherein the smooth surface is configured extend entirely over both the wound and a portion of intact epidermis around the wound.

21. The system of claim 11, wherein the moist tissue-interface layer comprises a water-based material, and wherein the water-based material is configured to extend entirely over the wound.

* * * * *